United States Patent
Simin et al.

(10) Patent No.: US 10,190,973 B2
(45) Date of Patent: Jan. 29, 2019

(54) INTEGRATED ULTRAVIOLET ANALYZER

(71) Applicant: Sensor Electronic Technology, Inc., Columbia, SC (US)

(72) Inventors: Grigory Simin, Columbia, SC (US); Michael Shur, Latham, NY (US); Alexander Dobrinsky, Loudonville, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/472,198

(22) Filed: Mar. 28, 2017

(65) Prior Publication Data

US 2017/0284933 A1 Oct. 5, 2017

Related U.S. Application Data

(60) Provisional application No. 62/316,535, filed on Mar. 31, 2016.

(51) Int. Cl.
*G01N 21/33* (2006.01)
*H01L 31/00* (2006.01)

(52) U.S. Cl.
CPC .................................. *G01N 21/33* (2013.01)

(58) Field of Classification Search
CPC .. G01N 21/33; G01N 21/64; G01N 33/54373; G01N 33/543; H01L 31/036; H01L 31/0324; H01L 31/02327; H01L 31/0322; H01L 31/0352

See application file for complete search history.

(56) References Cited

U.S. PATENT DOCUMENTS

| | | | |
|---|---|---|---|
| 6,147,756 A | 11/2000 | Zavracky et al. | |
| 6,690,042 B2 | 2/2004 | Khan et al. | |
| 6,841,809 B2 | 1/2005 | Fareed et al. | |
| 7,382,004 B2 | 6/2008 | Shur et al. | |
| 2002/0045272 A1* | 4/2002 | McDevitt | B01L 3/0289 436/518 |

(Continued)

FOREIGN PATENT DOCUMENTS

| | | |
|---|---|---|
| WO | 2009072056 A2 | 6/2009 |
| WO | 2009115847 A1 | 9/2009 |

OTHER PUBLICATIONS

Siemens, "Sirprocess UV600: Continuous gas analysis for UV-active gases," 2012, 4 pages.

(Continued)

*Primary Examiner* — David Porta
*Assistant Examiner* — Faye Boosalis
(74) *Attorney, Agent, or Firm* — LaBatt, LLC

(57) ABSTRACT

An integrated ultraviolet analyzer is described. The integrated ultraviolet analyzer can include one or more ultraviolet analyzer cells, each of which includes one or more ultraviolet photodetectors and one or more solid state light sources, which are monolithically integrated. The solid state light source can be operated to emit ultraviolet light, at least some of which passes through an analyzer active gap and irradiates a light sensing surface of the ultraviolet photodetector. A medium to be evaluated can be present in the analyzer active gap and affect the ultraviolet light as it passes there through, thereby altering an effect of the ultraviolet light on a ultraviolet photodetector.

20 Claims, 12 Drawing Sheets

(56) References Cited

U.S. PATENT DOCUMENTS

2005/0157301 A1    7/2005   Chediak et al.
2009/0242935 A1   10/2009   Fitzgerald

OTHER PUBLICATIONS

Worthington, et al., "Novel Differential Ultra-Violet Resonance Absorption Gas Analyzer for Nox Measurements in Continuous Emission Monitoring Systems," 15 pages.
International Application No. PCT/KR2017/003546, International Search Report and Written Opinion, dated Jul. 13, 2017, 10 pages.

\* cited by examiner

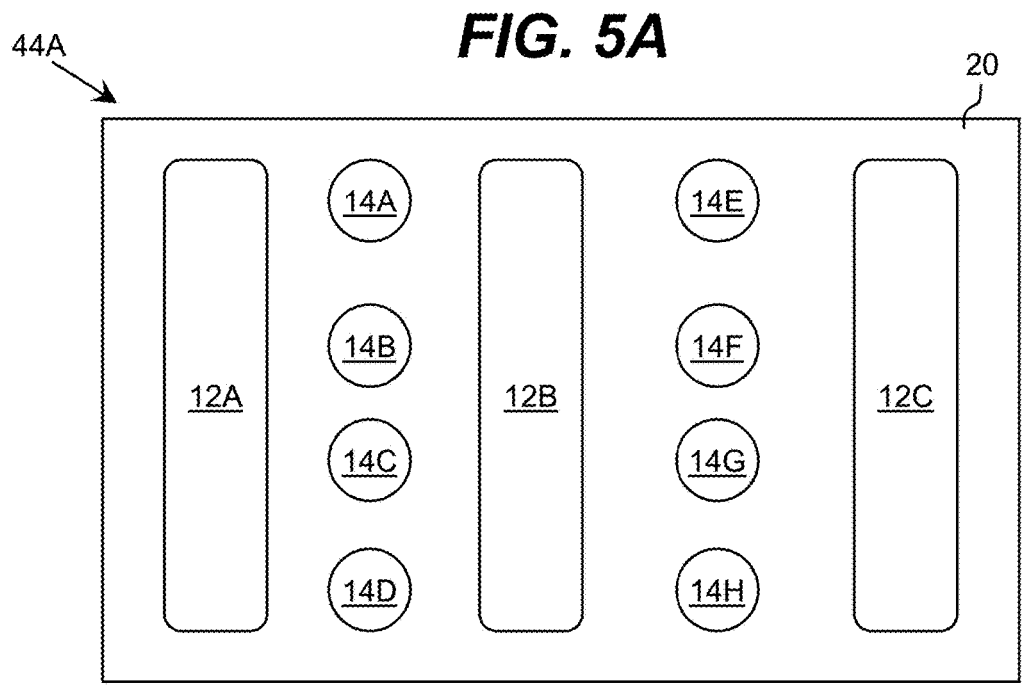
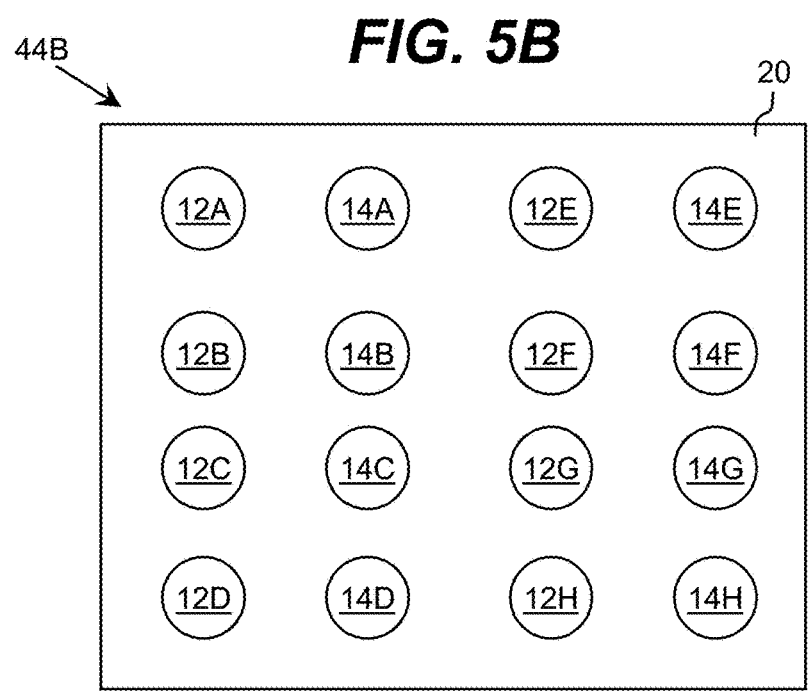

INTEGRATED ULTRAVIOLET ANALYZER

REFERENCE TO RELATED APPLICATIONS

The current application claims the benefit of U.S. Provisional Application No. 62/316,535, which was filed on 31 Mar. 2016, and which is hereby incorporated by reference.

TECHNICAL FIELD

The disclosure relates generally to ultraviolet analysis, and more particularly, to an integrated ultraviolet analyzer.

BACKGROUND ART

Chemical analysis using ultraviolet light is frequently achieved by radiating materials and measuring absorption or transmission in which radiation of different wavelengths is passed through to determine material identity and concentration. Ultraviolet (UV) analyzers are generally less specific than infrared (IR) or visible range analyzers. Additionally, UV analyzers are generally capable of more sensitivity than their IR counterparts—trace analyses are common for UV. Known solutions for UV analyzers typically include vacuum UV lamps, which require high voltage, high volume of the material needed for analysis and involve bulky and heavy equipment.

SUMMARY OF THE INVENTION

Aspects of the invention provide an integrated ultraviolet analyzer. The integrated ultraviolet analyzer can include one or more ultraviolet analyzer cells, each of which includes one or more ultraviolet photodetectors and one or more solid state light sources, which are monolithically integrated. The solid state light source can be operated to emit ultraviolet light, at least some of which passes through an analyzer active gap and irradiates a light sensing surface of the ultraviolet photodetector. A medium to be evaluated can be present in the analyzer active gap and affect the ultraviolet light as it passes there through, thereby altering an effect of the ultraviolet light on a ultraviolet photodetector.

A first aspect of the invention provides a n ultraviolet analyzer cell comprising: an ultraviolet photodetector; and a solid state light source configured to emit ultraviolet light, wherein at least some ultraviolet light emitted by the solid state light source passes through an analyzer active gap and irradiates a light sensing surface of the ultraviolet photodetector, wherein the ultraviolet photodetector and the solid state light source are monolithically integrated.

A second aspect of the invention provides an integrated ultraviolet analyzer comprising: a set of ultraviolet analyzer cells, each ultraviolet analyzer cell in the set of ultraviolet analyzer cells including: an ultraviolet photodetector; and a solid state light source configured to emit ultraviolet light, wherein at least some ultraviolet light emitted by the solid state light source passes through an analyzer active gap including a medium and irradiates a light sensing surface of the ultraviolet photodetector, wherein the ultraviolet photodetector and the solid state light source are monolithically integrated; and a circuit for operating the set of ultraviolet analyzer cells to evaluate the medium.

A third aspect of the invention provides an integrated ultraviolet analyzer comprising: an ultraviolet analyzer cell including: a substrate; an ultraviolet photodetector located on a first side of the substrate; and a solid state light source located on the first side of the substrate, wherein at least some ultraviolet light emitted by the solid state light source passes through an analyzer active gap and irradiates a light sensing surface of the ultraviolet photodetector; and a circuit for operating the ultraviolet analyzer cell to evaluate a medium present in the analyzer active gap.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 5A-5C show top views of illustrative structures including arrays of monolithically integrated ultraviolet analyzer cells according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
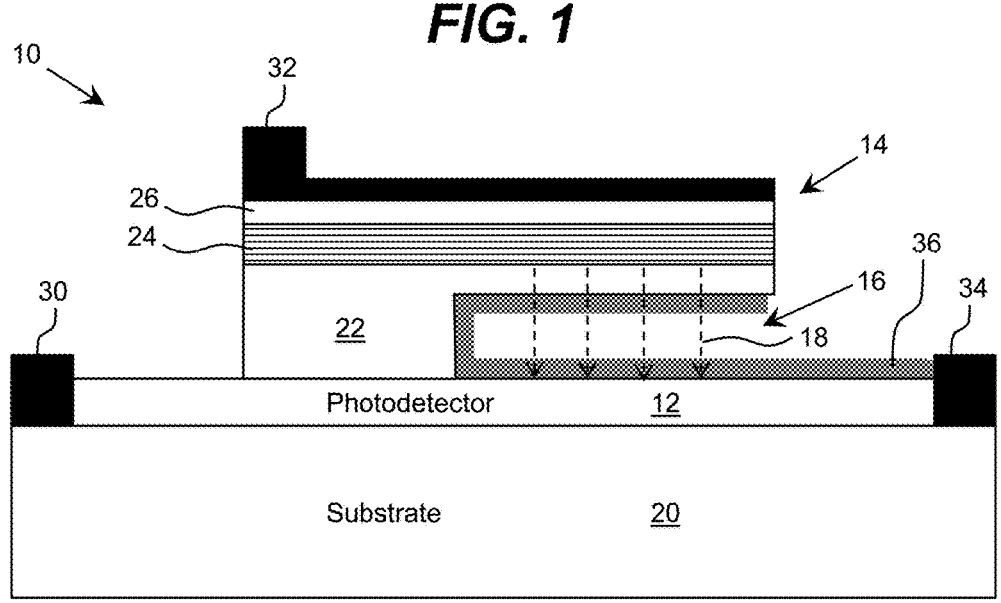
FIG. 1 shows an illustrative integrated ultraviolet analyzer cell according to an embodiment.

As indicated above, aspects of the invention provide an integrated ultraviolet analyzer. The integrated ultraviolet analyzer can include one or more ultraviolet analyzer cells, each of which includes one or more ultraviolet photodetectors and one or more solid state light sources, which are monolithically integrated. The solid state light source can be operated to emit ultraviolet light, at least some of which passes through an analyzer active gap and irradiates a light sensing surface of the ultraviolet photodetector. A medium to be evaluated can be present in the analyzer active gap and affect the ultraviolet light as it passes there through, thereby altering an effect of the ultraviolet light on a ultraviolet photodetector.

The integrated ultraviolet analyzer can be utilized to evaluate a gas. The entire analyzer can be small in size. For example, the analyzer active gap can be as small as a few (e.g., less than ten) micrometers or sub-micrometers. The small size can enable extremely high sensitivity of analysis of one or more attributes the medium (e.g., material, concentration, and/or the like). The solid state light source can have a relatively high modulation speed and the ultraviolet photodetector can have a fast response, which can enable fast measurements as well as accurate measurements of fast flowing fluids (e.g., gases) and other materials.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. As used herein, unless otherwise noted, terms of degree, such as "approximately," "substantially," and related terms, mean a reasonable amount of deviation from the stated value such that the end result is not significantly changed. For example, "approximately" can be inclusive of values within +/− ten percent of the stated value, while the term "substantially" can be inclusive of values within +/− five percent of the stated value, when such deviations would not negate the meaning of the value it modifies.

As also used herein, a structure is transparent when the structure allows at least ten percent of radiation having a target wavelength, which is radiated at a normal incidence to an interface of the structure, to pass there through. Furthermore, as used herein, a structure is reflective when the structure reflects at least ten percent of radiation having a target wavelength, which is radiated at a normal incidence to an interface of the structure. In an embodiment, the target wavelength of the radiation corresponds to a wavelength of radiation emitted or sensed (e.g., peak wavelength+/− five nanometers) by an active region of an optoelectronic device during operation of the device. For a given structure, the wavelength can be measured in a material of the structure and can depend on a refractive index of the material.

As used herein, monolithically integrated refers to two or more electronic devices that are located on the same substrate and are configured to operate together in an integrated manner. In an illustrative embodiment, each of the two or more electronic devices can be fabricated on the same substrate. Alternatively, one or more of the electronic devices can be bonded to a substrate. Furthermore, monolithically electronic devices include two or more electronic devices that are located on separate substrates, which are subsequently bonded together and configured in a manner that enables the two or more electronic devices to operate together in an integrated manner.

Turning to the drawings, FIG. 1 shows an illustrative integrated ultraviolet analyzer cell 10 according to an embodiment. As used herein, a "cell" comprises a group of electronic devices that are operated together in a circuit. The analyzer cell 10 includes an ultraviolet (UV) photodetector 12 and an ultraviolet solid state light source (UV SSLS) 14. The UV photodetector 12 and the UV SSLS 14 are included in a single structure, which includes an analyzer active gap 16 between a portion of the UV photodetector 12 and a portion of the UV SSLS 14. During operation of the analyzer cell 10, the UV SSLS 14 generates ultraviolet light 18, at least some of which irradiates at least some of the analyzer active gap 16 and a surface of the UV photodetector 12. By analyzing changes in an effect of the ultraviolet light 18 on the UV photodetector 12, the analyzer 10 can evaluate one or more attributes of a medium, such as a fluid, located within the analyzer active gap 16.

The UV photodetector 12 can comprise any type of semiconductor device having an electric output affected by the incident ultraviolet light 18. Illustrative UV photodetectors 12 include a p-n junction diode, a multiple quantum well diode, a reverse-biased SSLS (e.g., a light emitting diode, laser diode, and/or the like), a photoresistor, and/or the like. The UV SSLS 14 can comprise any type of ultraviolet light emitting SSLS. For example, the UV SSLS 14 can be a light emitting diode, a laser, a laser diode, and/or the like.

In an embodiment, the analyzer cell 10 can be fabricated on a substrate 20. The substrate 20 can comprise any type of substrate 20 suitable for fabrication of the analyzer cell 10 thereon. In a more particular embodiment, the analyzer cell 10 can be formed of a single semiconductor heterostructure grown on the substrate 20. In this case, the analyzer cell 10 can include a set of semiconductor layers forming the UV photodetector 12, a n-type layer 22 (e.g., a cladding layer, electron supply layer, contact layer, and/or the like) located on the UV photodetector 12, a light generating structure 24 (e.g., a multiple quantum well structure) located on the n-type layer 22, and a p-type layer 26 (e.g., a cladding layer, hole supply layer, contact layer, and/or the like) located on the light generating structure 24. While not shown for clarity, it is understood that the analyzer cell 10 can include one or more additional semiconductor layers.

Fabrication of the analyzer cell 10 can include growth of the semiconductor layers forming the UV photodetector 12 and UV SSLS 14, followed by formation of the analyzer active gap 16 by removing some of the semiconductor material. As illustrated, the analyzer active gap 16 can be substantially parallel to a surface of the substrate 20 on which the semiconductor layers are fabricated. In an embodiment, a portion of a n-type layer 22 of the UV SSLS 14 can be removed to form the analyzer active gap 16. The analyzer active gap 16 can be formed using any solution. For example, the material can be removed by selective etching. In another embodiment, an epitaxial overgrowth approach can be utilized as is known in art.

In a more particular illustrative embodiment, the analyzer cell 10 is a group III-V materials based device, in which some or all of the various layers are formed of elements selected from the group III-V materials system. In a still more particular illustrative embodiment, the various layers of the analyzer cell 10 are formed of group III nitride based materials. Group III nitride materials comprise one or more group III elements (e.g., boron (B), aluminum (Al), gallium (Ga), and indium (In)) and nitrogen (N), such that $B_WAl_XGa_YIn_ZN$, where $0 \leq W, X, Y, Z \leq 1$, and $W+X+Y+Z=1$. Illustrative group III nitride materials include binary, ternary and quaternary alloys such as, AlN, GaN, InN, BN, AlGaN, AlInN, AlBN, AlGaInN, AlGaBN, AlInBN, and AlGaInBN with any molar fraction of group III elements.

An illustrative embodiment of a group III nitride based analyzer cell 10 includes a light generating region 24 composed of $In_yAl_xGa_{1-x-y}N$, $Ga_zIn_yAl_xB_{1-x-y-z}N$, an $Al_xGa_{1-x}N$ semiconductor alloy, or the like. Similarly, the n-type layer 22 and the p-type layer 26 can be composed of an $In_yAl_xGa_{1-x-y}N$ alloy, a $Ga_zIn_yAl_xB_{1-x-y-z}N$ alloy, or the like. The molar fractions given by x, y, and z can vary between the various layers 22, 24, and 26. The UV photodetector 12 also can include one or more group III nitride layers. For example, the UV photodetector 12 can include a similar structure as shown for the ultraviolet SSLS 14 with the order of the semiconductor layers reversed. In this case, either the ultraviolet SSLS 14 or the UV photoconductor 12 can be operated to generate the ultraviolet radiation, while the other is operated to sense the radiation.

The substrate 20 can be formed of any suitable material including, for example, sapphire, silicon carbide (SiC), silicon (Si), bulk GaN, bulk AlN, bulk or a film of AlGaN, bulk or a film of BN, AlON, LiGaO$_2$, LiAlO$_2$, aluminum oxinitride (AlO$_x$N$_y$), MgAl$_2$O$_4$, GaAs, Ge, or another suitable material. Furthermore, the substrate 20 can be a conducting or insulating material. While the UV photoconductor 12 is shown located directly on the substrate 20 and the ultraviolet SSLS 14 is shown on the UV photodetector 12, it is understood that this is only illustrative, and an alternative embodiment can comprise an analysis cell with an ultraviolet SSLS located directly on the substrate 20 and the UV photodetector 12 located on the ultraviolet SSLS. While group III nitride materials are used to illustrate aspects of the invention, it is understood that the invention is not limited to such materials and embodiments can be made from any other suitable semiconductor materials.

The analyzer cell 10 can further include various contacts for integrating the analyzer cell 10 into a circuit. To this extent, the analyzer cell 10 can include a common contact 30, a SSLS bias contact 32, and a photodetector bias contact 34. In an embodiment, the common contact 30 comprises a n-type contact for both the UV photodetector 12 and the UV SSLS 14, while the bias contacts 32, 34 are p-type contacts for the respective devices. Each contact 30, 32, 34 can include one or more metal layers. As illustrated, the SSLS bias contact 32 can extend across the surface of the p-type layer 26 of the UV SSLS 14. In this case, the SSLS bias contact 32 can be reflective of the ultraviolet radiation 18, thereby directing additional ultraviolet radiation 18 toward the analyzer active gap 16.

As described herein, the analyzer cell 10 can evaluate a medium located within the analyzer active gap 16. When the medium can comprise one or more aggressive chemicals, the analyzer cell 10 can include an insulating layer 36 covering the exposed surfaces of the analyzer cell 10 in the analyzer active gap 16. The insulating layer 36 can comprise any suitable material that is both transparent to the ultraviolet radiation generated by the UV SSLS 14 and can is resistant to breakdown in the presence of the medium. In an illustrative embodiment, the insulating layer 36 is at least thirty percent transparent as measured for radiation directed normal to a surface of the insulating layer 36. Illustrative materials for the insulating layer 36 include a fluoropolymer, silicon dioxide, sapphire, calcium fluoride (CaF$_2$), magnesium fluoride (MgF$_2$), etc. In an embodiment, the insulating layer 36 can be configured to provide light guiding for the ultraviolet radiation 18. For example, the insulating layer 36 can have a surface texture, which is configured to direct the ultraviolet radiation 18 out of or into the insulating layer 36 toward a surface of the photodetector 12.

Figure 2:
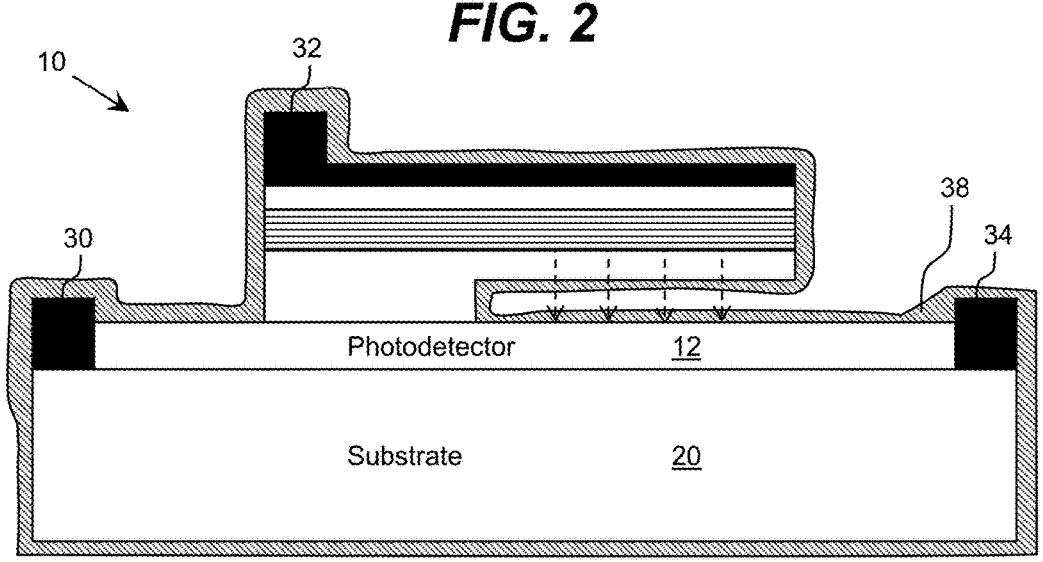
FIG. 2 shows another illustrative integrated ultraviolet analyzer cell according to an embodiment.

FIG. 2 shows another illustrative integrated ultraviolet analyzer cell 10 according to an embodiment. In this case, the analyzer cell 10 is configured in the same manner as shown and described in conjunction with FIG. 1. However, the analyzer cell 10 is protected from an ambient environment by an encapsulant 38. The encapsulant 38 can surround all external surfaces of the analyzer cell 10 and can be included in applications in which an aggressive chemical may be present in an ambient environment in which the analyzer cell 10 is located. While not shown for clarity, it is understood that the encapsulant 38 can be pierced in order to obtain electrical contact with each of the contacts 30. 32, 34.

Figure 3:
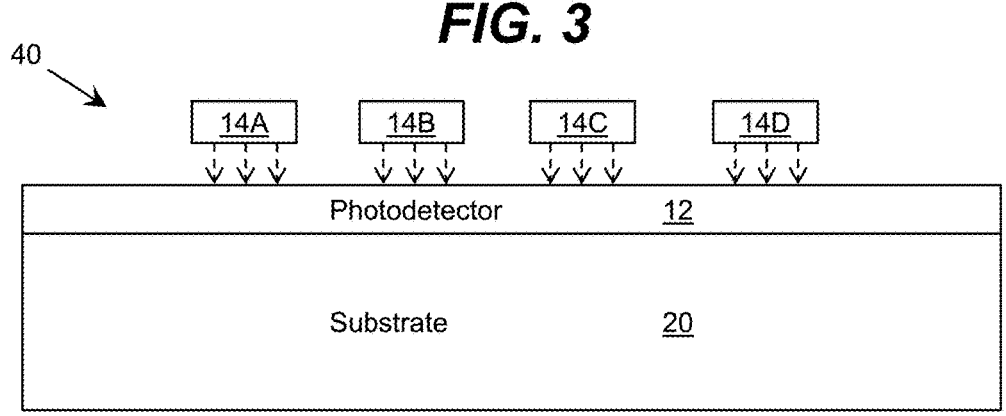
FIG. 3 shows a schematic view of an illustrative ultraviolet analyzer cell including multiple UV SSLSs according to an embodiment.

An embodiment of an ultraviolet analyzer cell described herein can include multiple UV SSLSs. For example, FIG. 3 shows a schematic view of an illustrative ultraviolet analyzer cell 40 including multiple UV SSLSs 14A-14D according to an embodiment. While not shown, each UV SSLS 14A-14D can be fabricated as shown in FIG. 1, in which each UV SSLS 14A-14D comprises a mesa supported by the photodetector 12 with a portion removed to form the active gap. As illustrated, each UV SSLS 14A-14D can emit ultraviolet radiation that is directed onto a surface of a photodetector 12 through the corresponding active gap. Multiple UV SSLSs 14A-14D can be utilized, for example, to increase a total active area for analysis of the medium. In this case, a corresponding circuit can operate all of the UV SSLSs 14A-14D as a group. Alternatively, the circuit can be configured to operate the UV SSLSs 14A-14D individually, in sub-groups, and/or the like, which can be selected, for example, based on a desired accuracy of the evaluation.

In another embodiment, the group of UV SSLSs 14A-14D generate ultraviolet light having multiple distinct peak emission wavelengths. For example, each UV SSLS 14A-14D can generate ultraviolet light having a different peak wavelength from that of every other UV SSLS 14A-14D. Alternatively, the UV SSLSs 14A-14D can include sub-groups of UV SSLSs, in which each sub-group generates ultraviolet light having a common peak wavelength that differs from the peak wavelength of the other sub-groups. In either case, the difference exceeds any difference in peak wavelengths due to the limits of manufacturing techniques. UV SSLSs 14A-14D emitting ultraviolet light with different peak wavelengths can be fabricated using any solution. For example, the UV SSLSs 14A-14D can have differing attributes in the respective light generating regions 24 (FIG. 1). Illustrative attributes include quantum wells formed of different materials than the quantum wells of other light generating regions 24, quantum wells and/or barriers having different thicknesses than those of the quantum wells and/or barriers of other light generating regions 24, and/or the like.

Figure 4:
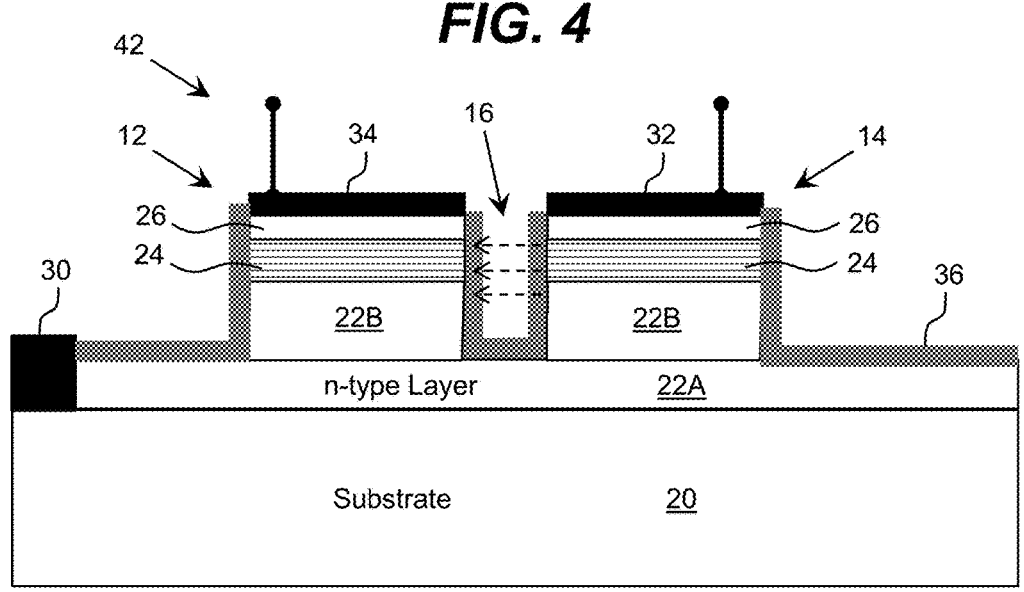
FIG. 4 shows a schematic cross-section of an illustrative ultraviolet analyzer cell according to another embodiment of the invention.

In an alternative embodiment, an ultraviolet analyzer cell can include an analyzer active gap that is oriented substantially perpendicular to the substrate 20. For example, FIG. 4 shows a schematic cross-section of an illustrative ultraviolet analyzer cell 42 according to another embodiment of the invention. In this case, the ultraviolet analyzer cell 42 includes an UV photodetector 12 and an UV SSLS 14, each of which comprises a mesa separated by an analyzer active gap 16. In the embodiment illustrated, the UV photodetector 12 and the UV SSLS 14 can have the same layer structure. In this case, the mesa acting as the UV photodetector 12 can be operated in reverse bias. To this extent, determination of which structure corresponds to the UV photodetector 12 and which structure corresponds to the UV SSLS 14 is dependent on how the ultraviolet analyzer cell 42 is connected in a circuit, and can be changed. However, it is understood that this configuration is only illustrative and in other embodiments the photodetector 12 can have a different layer structure than that of the UV SSLS 14 and comprise a different type of device, such as a p-n diode, p-i-n diode, photoresistor, etc.

The UV photodetector 12 and the UV SSLS 14 can be fabricated over a substrate 20 using any solution. For example, fabrication of the ultraviolet analyzer cell 42 can include growing a first n-type layer 22A on the substrate, growing a second n-type layer 22B on the first n-type layer 22A, growing a light generating region 24 on the second n-type layer 22B, and growing a p-type layer 26 on the light generating region 24. Subsequently, the semiconductor structure can be etched to form a substantially vertical analyzer active gap 16, which extends to a surface of the first n-type layer 22A. While the n-type layers 22A, 22B are described as different layers, it is understood that the n-type layers 22A, 22B can be formed of the same material.

Fabrication of the ultraviolet analyzer cell 42 can include formation of the contacts 30, 32, 34 as described herein. Furthermore, one or more surfaces of the ultraviolet analyzer cell 42 can be covered with an insulating layer 36 as described herein. During operation of the analyzer cell 42, a ground voltage bias can be applied to contact 30, while a positive voltage bias can be applied to contact 34, and a negative voltage bias can be applied to contact 32. In this manner, the UV photodetector 12 can operate in reverse bias while the UV SSLS 14 operates in forward bias.

Figure 5C:
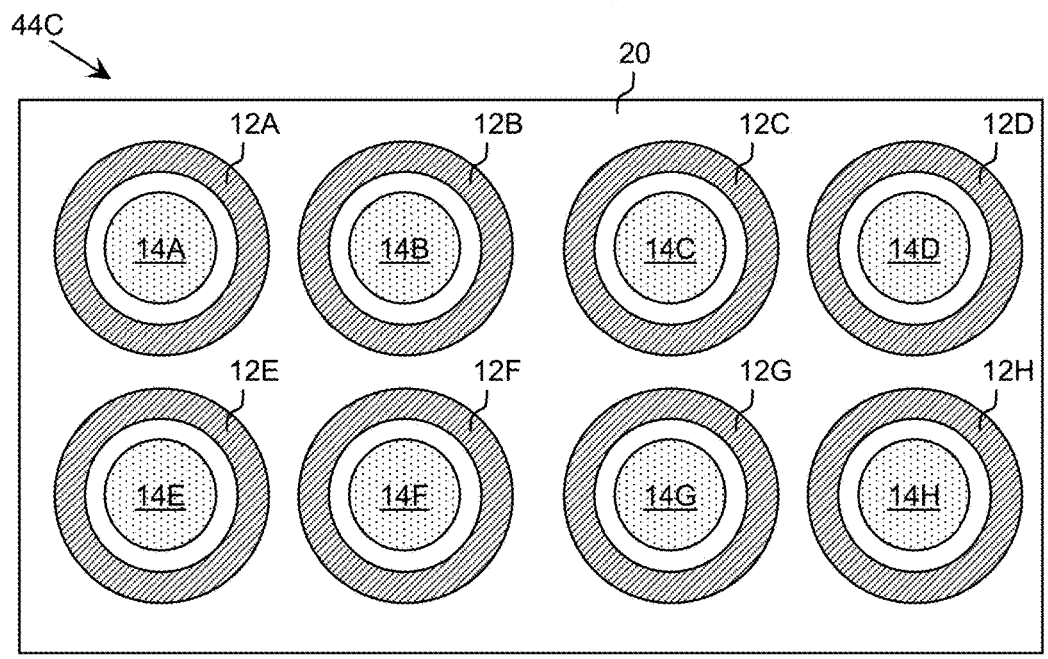

The structure shown for the ultraviolet analyzer cell 42 can be utilized to make a structure including multiple ultraviolet analyzer cells, each of which includes a set of UV photodetectors 12 and a set of UV SSLSs 14. For example, FIGS. 5A-5C show top views of illustrative structures 44A-44C, respectively, including arrays of monolithically integrated ultraviolet analyzer cells according to embodiments. As illustrated in FIG. 5A, the structure 44A includes three elongate UV photodetectors 12A-12C alternating with two arrays of UV SSLSs 14A-14D and 14E-14H. In this configuration, the arrays of UV SSLSs 14A-14D and 14E-14H can emit ultraviolet light that irradiates the UV photodetectors located on both sides of each array. For example, the array of UV SSLSs 14A-14D can irradiate both the UV photodetectors 12A, 12B, while the array of UV SSLSs 14E-14H can irradiate both the UV photodetectors 12B, 12C.

In FIG. 5B, the structure 44B is shown including two arrays of UV photodetectors 12A-12D and 12E-12H alternating with two arrays of UV SSLSs 14A-14D and 14E-14H. In this case, a photodetector can be irradiated by multiple distinct UV SSLSs. In FIG. 5C, the structure 44C includes an array of UV SSLSs 14A-14H, each of which is surrounded by a UV photodetector 12A-12H. In this arrangement, the UV photodetectors can more efficiently absorb the ultraviolet light emitted by the corresponding UV SSLSs.

Use of multiple UV SSLSs and/or multiple UV photodetectors can, for example, increase a total active area for analysis of the medium. A corresponding circuit can operate all of the UV SSLSs and/or UV photodetectors as a group. Alternatively, the circuit can be configured to operate the UV SSLSs and/or UV photodetectors individually, in subgroups, and/or the like, which can be selected, for example, based on a desired accuracy of the evaluation. In another embodiment, the UV SSLSs generate ultraviolet light having multiple distinct peak emission wavelengths. For example, each UV SSLS can generate ultraviolet light having a different peak wavelength from that of every other UV SSLS. Alternatively, the UV SSLSs can include subgroups of UV SSLSs, in which each sub-group generates ultraviolet light having a common peak wavelength that differs from the peak wavelength of the other sub-groups. In either case, the difference exceeds any difference in peak wavelengths due to the limits of manufacturing techniques.

While various UV SSLSs and UV photodetectors are shown as having circular shapes, it is understood that this is only illustrative and the UV SSLSs and UV photodetectors can have any suitable shape. Similarly, while each structure 44A-44C is shown including a particular number and arrangement of UV SSLSs and UV photodetectors, it is understood that these are only illustrative and embodiments can include any of various differing arrangements and numbers of UV SSLSs and UV photodetectors.

Figure 6A:
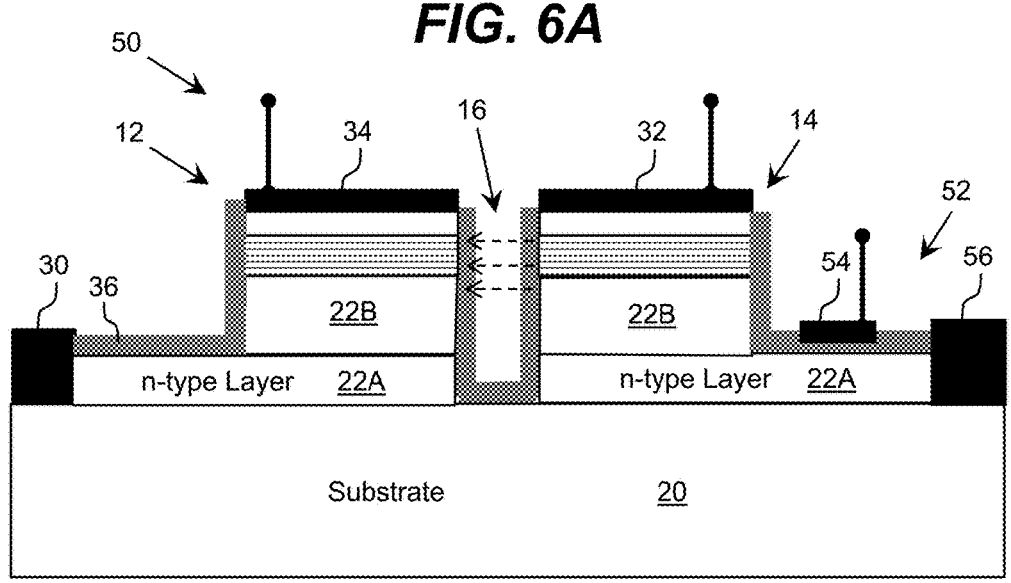
FIGS. 6A and 6B show schematics of illustrative ultraviolet analyzer cells with an integrated transistor according to embodiments.
Figure 6B:
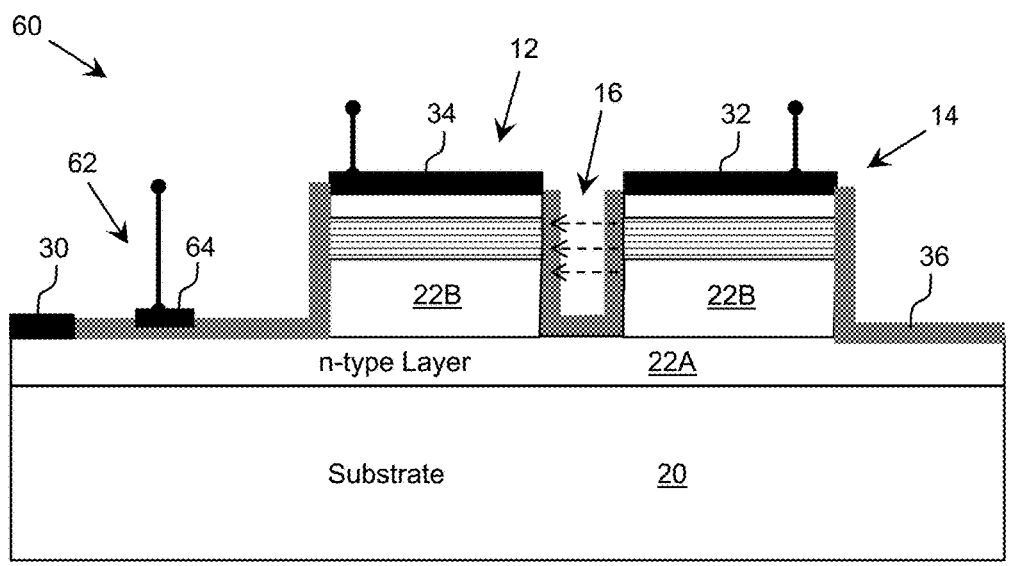

In addition to a monolithically integrated UV SSLS and UV photodetector, an ultraviolet analyzer cell described herein can be monolithically integrated with one or more additional components of a circuit. For example, FIGS. 6A and 6B show schematics of illustrative ultraviolet analyzer cells 50, 60, each with an integrated transistor 52, 62, respectively, according to an embodiment. In FIG. 6A, the analyzer cell 50 is configured similar to the analyzer cell 42 shown in FIG. 4. However, the analyzer active gap 16 extends through the n-type layer 22A, thereby electrically isolating the UV photodetector 12 and the US SSLS 14. The n-type layer 22A extends beyond the UV SSLS 14 and the integrated transistor 52 is formed on a surface of the n-type layer 22A. In particular, a gate 54 of the transistor 52 is formed over the surface of the n-type layer 22A between the UV SSLS 14 and a source contact 56 for the transistor 52. As illustrated, the gate 54 can be located on the insulating layer 36 to provide an insulated gate. The transistor 52 can be operated to provide electrical modulation of the signal applied to the SSLS bias contact 32.

FIG. 6B shows a schematic of an illustrative ultraviolet analyzer cell 60 with an integrated transistor 62 according to another embodiment. In this case, the analyzer cell 60 is configured similar to the analyzer cell 42 shown in FIG. 4. However, the integrated transistor 62 is formed on a surface of the n-type layer 22A. In particular, a gate 64 of the transistor 62 is formed over the surface of the n-type layer 22A on the insulating layer 36 located between the common contact 30 and the UV photodetector 12. The common contact 30 can be utilized as a drain contact for the transistor 62. In an embodiment, the gate 64 can be electrically connected to the photodetector bias contact 34. The transistor 62 can provide amplification and/or transformation of the signal obtained from the photodetector bias contact 34.

While each of the ultraviolet analyzer cells 50, 60 is shown including a monolithically integrated transistor, it is understood that alternative and/or additional electronic components can be monolithically integrated or included in a corresponding circuit. For example, a circuit including the ultraviolet analyzer cell 50 may include multiple transistors or other electronic components to form the signal modulator. Similarly, another type of electronic component can be utilized to provide amplification and/or transformation of the signal obtained from the photodetector bias contact 34.

Figure 7:
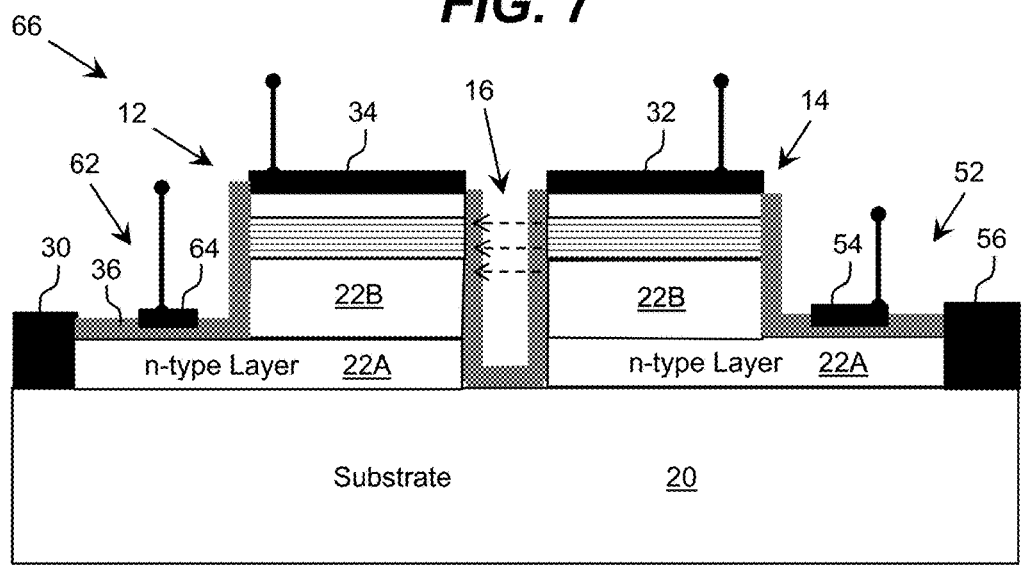
FIG. 7 shows a schematic of an illustrative ultraviolet analyzer cell with multiple integrated transistors according to another embodiment.

Additionally, it is understood that an embodiment can include monolithically integrated electronic components for both the UV SSLS 14 and the UV photodetector 12. For example, an embodiment can include both the monolithically integrated transistors 52, 62. To this extent, FIG. 7 shows a schematic of an illustrative ultraviolet analyzer cell 66 with multiple integrated transistors 52, 62 according to another embodiment. In particular, as illustrated, the analyzer active gap 16 can extend through the n-type layer 22A, thereby electrically isolating the UV photodetector 12 and the UV SSLS 14. The transistors 52, 62 can be operated as discussed herein. Using an ultraviolet analyzer cell described herein, such as the ultraviolet analyzer cell 66, high frequency (e.g., Gigahertz) ultraviolet radiation modulation is possible. In this case, the UV photodetector 12 also can measure fluorescence when the medium fluoresces in response to ultraviolet light.

Figure 8:
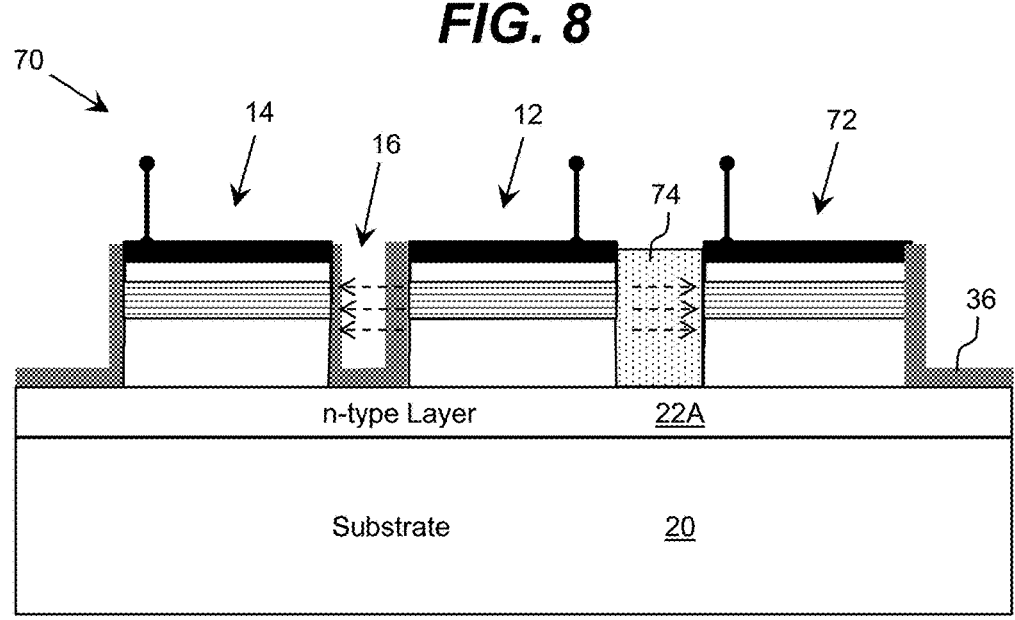
FIG. 8 shows an illustrative ultraviolet analyzer cell including a differential pair of UV photodetectors according to an embodiment.

As discussed herein, a medium is evaluated based on an effect of ultraviolet light impacting the UV photodetector. In an embodiment, an ultraviolet analyzer cell can use a difference between a known effect and the effect of the ultraviolet light passing through the medium to evaluate the medium. For example, FIG. 8 shows an illustrative ultraviolet analyzer cell 70 including a differential pair of UV photodetectors 14, 72 according to an embodiment. In this case, the analyzer cell 70 includes an UV SSLS 14, which emits ultraviolet light that passes through a medium and impacts an UV photodetector as described herein.

Additionally, the analyzer cell 70 includes a second UV photodetector 72 that is irradiated by ultraviolet light emitted from the UV SSLS 14 through a gap filling material 74. The gap filling material 74 can completely fill the gap between the UV SSLS 14 and the UV photodetector 72 to prevent any of the medium from being present therein. The gap filling material 74 can comprise any type of material that is transparent to the ultraviolet light. Additionally, the gap filling material 74 can be resistant to breakdown in the presence of the medium (e.g., a chemical present therein). In an embodiment, the gap filling material 74 is the same material as that utilized for the insulating layer 36 (e.g., a fluoropolymer, silicon dioxide, sapphire, $CaF_2$, $MgF_2$, and/or the like).

During operation of the analyzer cell 70, the UV SSLS 14 emits ultraviolet light that contacts both the UV photodetectors 14, 72. The respective effects on the UV photodetectors 14, 72 are measured and evaluated to evaluate one or more attributes of a medium present in the gap 16. For example, a difference in the effects (e.g., a difference in the output signals) can be calculated and used to evaluate the medium. By using a differential signal, the evaluation can be less sensitive to other factors that may affect the output signal of the UV photodetector 12, such as a variation in temperature, external illumination, and/or the like.

Figure 9A:
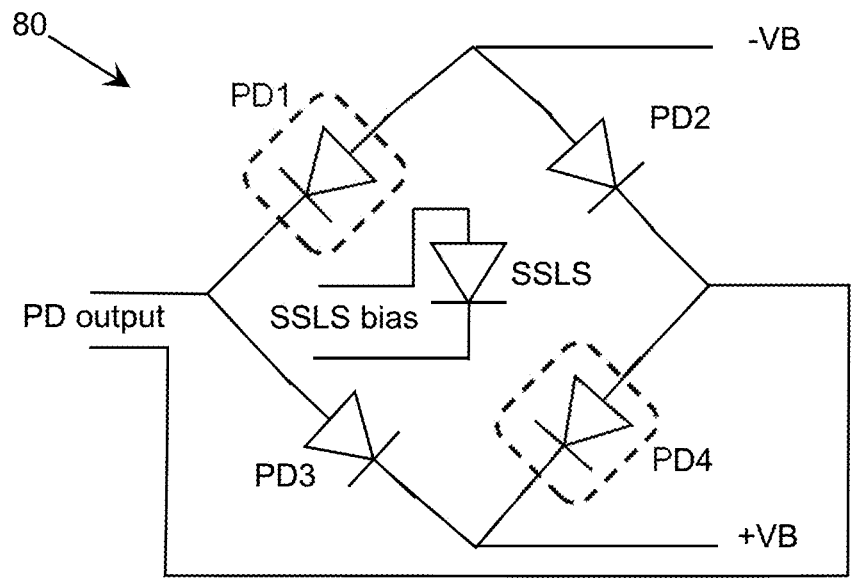
FIGS. 9A and 9B show illustrative circuits providing a differential photodetector output according to embodiments.
Figure 9B:
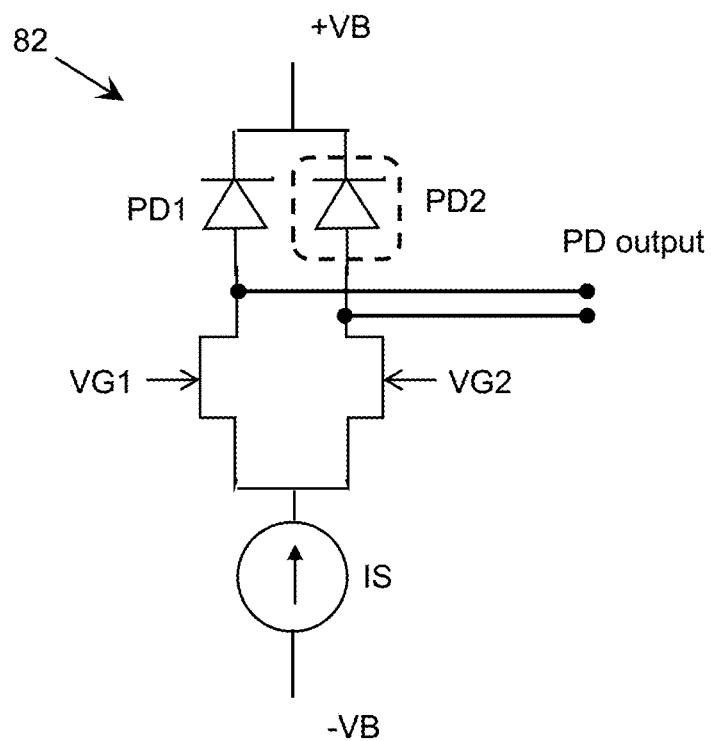

FIGS. 9A and 9B show illustrative circuits 80, 82 providing a differential output according to embodiments. In FIG. 9A, the circuit 80 includes a single SSLS with four photodetectors (PD1-PD4) connected in a bridge type circuit in which the photodetectors PD1-PD4 are reverse biased. In an embodiment, the ultraviolet light that reaches the photodetectors PD2, PD3 passes through a medium to be analyzed, while the ultraviolet light that reaches the photodetectors PD1, PD4 is protected from the medium (e.g., passes through a gap filling material). In this case, the differential output can be obtained from the electrical connection between the photodetectors PD1, PD3 and the electrical connection between the photodetectors PD2, PD4.

In FIG. 9B, the circuit 82 includes a pair of photodetectors PD1, PD2 connected into a differential amplifier circuit with a pair of transistors (e.g., field-effect transistors or bipolar transistors). While not shown for clarity, the circuit can include a SSLS configured to emit ultraviolet light that irradiates both photodetectors PD1, PD2. In an embodiment, the ultraviolet light that reaches the photodetector PD1 passes through a medium to be analyzed, while the ultraviolet light that reaches the photodetector PD2 is protected from the medium (e.g., passes through a gap filling material).

Figure 10A:
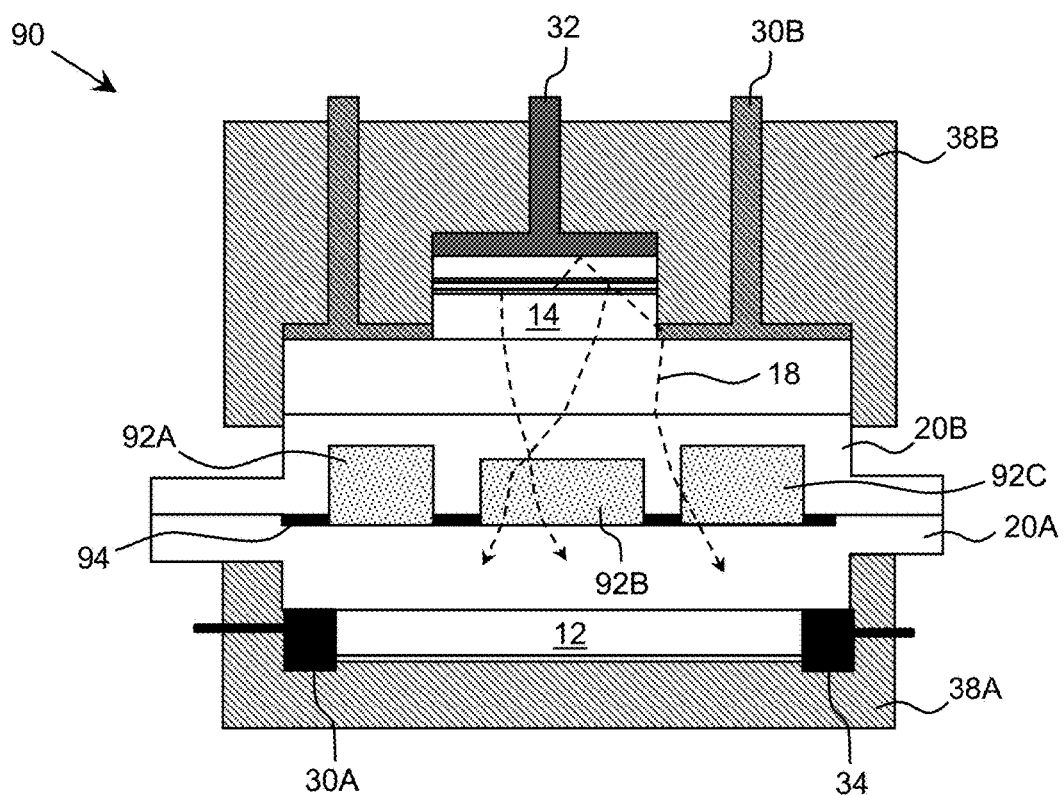
FIGS. 10A and 10B show side and perspective views of an illustrative ultraviolet analyzer cell fabricated using wafer bonding according to an embodiment.
Figure 10B:
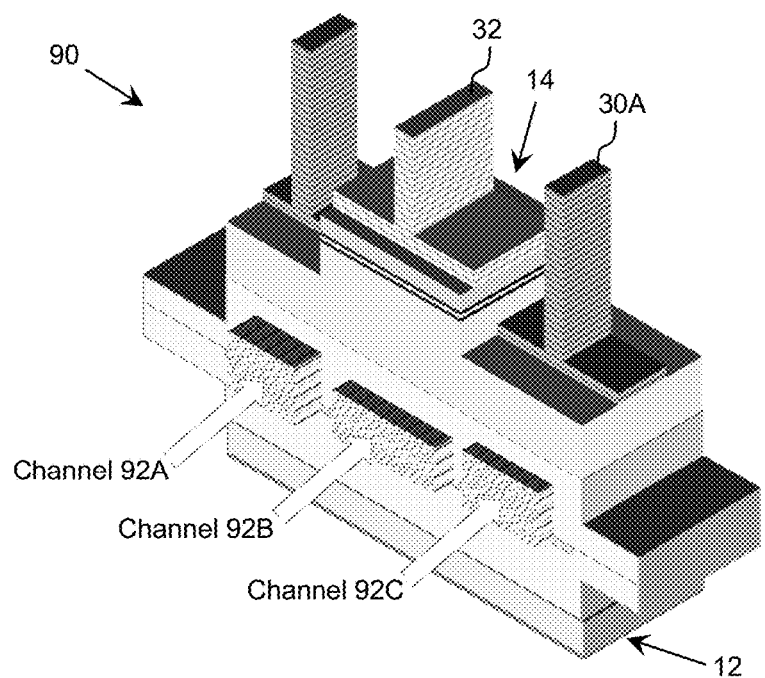

While embodiments of the ultraviolet analyzer cell can be fabricated by growth of the semiconductor layers forming the UV photodetector(s) and UV SSLS(s) on the same substrate, it is understood that this is only illustrative, and embodiments of the ultraviolet analyzer cell can be fabricated using a different solution. For example, FIGS. 10A and 10B show side and perspective views of an illustrative ultraviolet analyzer cell 90 fabricated using wafer bonding according to an embodiment. In this case, an UV photodetector 12 can be fabricated on a first substrate 20A using any solution. The UV photodetector 12 can include a source contact 30A and a drain contact 34, and can be protected from an ambient environment by an encapsulant 38A. Similarly, an UV SSLS 14 can be fabricated on a second substrate 20B using any solution. The UV SSLS 14 can include a p-type contact 32, a n-type contact 30B, and can be protected from an ambient environment by an encapsulant 38B.

The substrates 20A, 20B can be wafer bonded to each other such that ultraviolet light 18 emitted by the UV SSLS 14 is directed through the substrates 20A, 20B and irradiates the UV photodetector 12. To this extent, each substrate 20A, 20B can comprise a material transparent to the ultraviolet light 18. In an illustrative embodiment, the substrates 20A, 20B are formed of sapphire. To facilitate evaluation of a medium, the analyzer active gap can be formed by one or more channels 92A-92C, each of which can be formed in one or both of the substrates 20A, 20B using any solution. For example, prior to wafer bonding (and/or growth of a corresponding device), one or both substrates 20A, 20B can be etched to create openings for the channels 92A-92C. To reduce an amount of ultraviolet light 18 that does not pass through any of the channels 92A-92C from irradiating the UV photodetector 12, an ultraviolet reflective material 94 can be deposited in regions of the interface of the substrates 20A, 20B adjacent to the channels 92A-92C. The ultraviolet reflective material 94 can comprise any type of reflective material, such as polished aluminum, a fluoropolymer such as polytetrafluoroethylene (PTFE), a reflective polymer (e.g., Teflon), and/or the like. In an embodiment, the reflective material 94 is an ultraviolet reflective substrate, which is wafer bonded to one of the substrates 20A, 20B. In this case, the reflective material 94 can be bonded and subsequently etched to form the channels 92A-92C.

During operation, the medium can be present within the channels 92A-92C, thereby affecting the ultraviolet radiation 18 irradiating the UV photodetector 12. In an embodiment, the medium flows through the channels 92A-92C. While only a single UV photodetector 12 and UV SSLS 14 are shown, it is understood that embodiments can include any number of UV photodetectors 12 and UV SSLSs 14. For example, a channel 92A-92C can include an array of UV photodetectors 12 and UV SSLSs 14. Alternatively, each channel 92A-92C can include on or more different UV photodetectors 12 and UV SSLSs 14. In either case, the UV SSLSs 14 can be configured to emit ultraviolet radiation having different peak wavelengths. For example, a medium flowing through one channel (or a group of channels) may be irradiated by one or more UV SSLSs emitting ultraviolet light having a first peak wavelength, while a medium flowing through another channel (or a group of channels) may be irradiated by one or more UV SSLSs emitting ultraviolet light having a second peak wavelength different from the first peak wavelength. Such a configuration can improve an accuracy of the analysis and identification of the composition of the medium.

Figure 11:
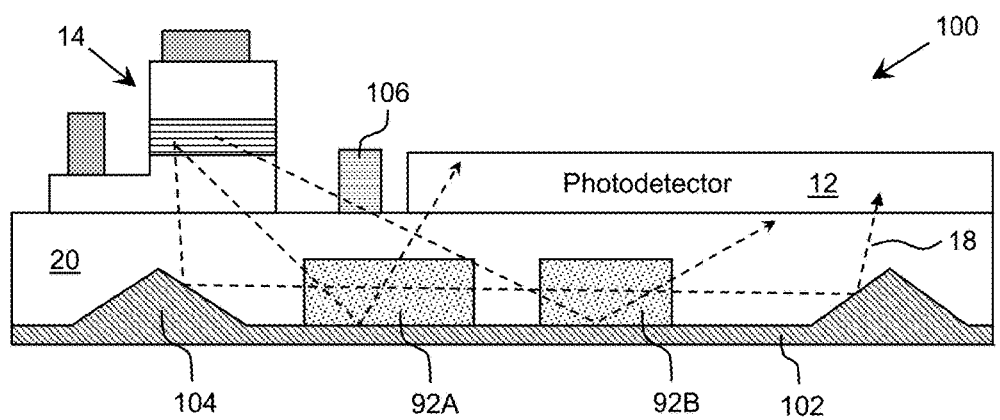
FIG. 11 shows an illustrative ultraviolet analyzer cell with channels according to an embodiment.

An embodiment of an ultraviolet analyzer cell can include one or more channels when the UV SSLS(s) and UV photodetectors are located on the same substrate. For example, FIG. 11 shows an illustrative ultraviolet analyzer cell 100 with an analyzer active gap formed from channels 92A, 92B according to an embodiment. In this case, the analyzer cell 100 includes a UV photodetector 12 and a UV SSLS 14, each of which is located on a first side of a substrate 20. Channels 92A, 92B are formed on the second side of the substrate 20 and can include a medium to be evaluated (e.g., which can be flowing through the channels 92A, 92B). An ultraviolet reflective surface 102 is formed on (e.g., wafer bonded to) the second side of the substrate 20. The reflective surface 102 can include a set of mirror elements 104, which can be configured to direct ultraviolet light 18 emitted by the UV SSLS 14 toward the photodetector 12.

During operation of the ultraviolet analyzer cell 100, the UV SSLS 14 can emit ultraviolet light that is directed into the substrate 20 (e.g., a sapphire substrate) and through one or more of the channels 92A, 92B. The ultraviolet light can be reflected by the reflective surface 102 and directed toward the photodetector 12. Analysis of an effect of the ultraviolet light 18 on the photodetector 12 can evaluate the medium present within the channels 92A, 92B. As illustrated, the analyzer cell 100 can further include a thermistor 106, which can provide temperature data during operation of the analyzer cell 100. The temperature data can be used to account for differences in the photodetector 12, which are due to temperature and not to the content of the medium present within the channels 92A, 92B.

Figure 12:
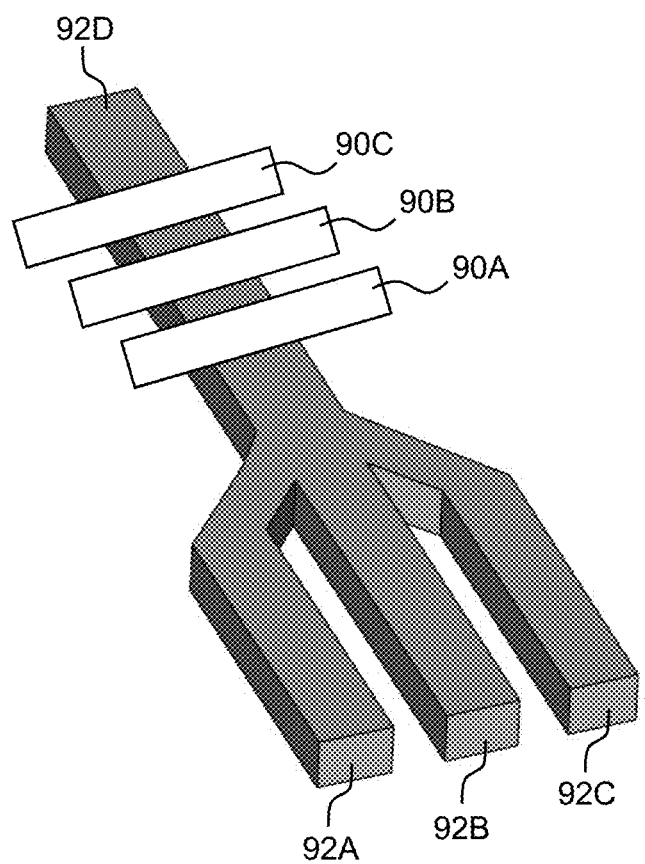
FIG. 12 shows an illustrative network of connecting channels according to an embodiment.

In an embodiment, multiple channels described herein can form a network of connecting channels. Such a network can enable the combination of multiple distinct media into a single channel. The media can be evaluated prior to combining and/or after combining. For example, FIG. 12 shows an illustrative network of connecting channels according to an embodiment. As illustrated, three channels 92A-92C can merge into a single channel 92D. Multiple ultraviolet analyzer cells 90A-90C are shown located along the channel 92D. In an embodiment, each channel 92A-92C can include a different medium (e.g., a chemical) that are concurrently delivered to the channel 92D. The chemicals can undergo a reaction within the channel 92D, the progress of which can be monitored by the ultraviolet analyzer cells 90A-90C. For example, as the chemical reaction(s) progress(es), the levels of absorption of ultraviolet light can vary. Such a change can be detected by the ultraviolet analyzer cells 90A-90C and analyzed.

Figure 13:
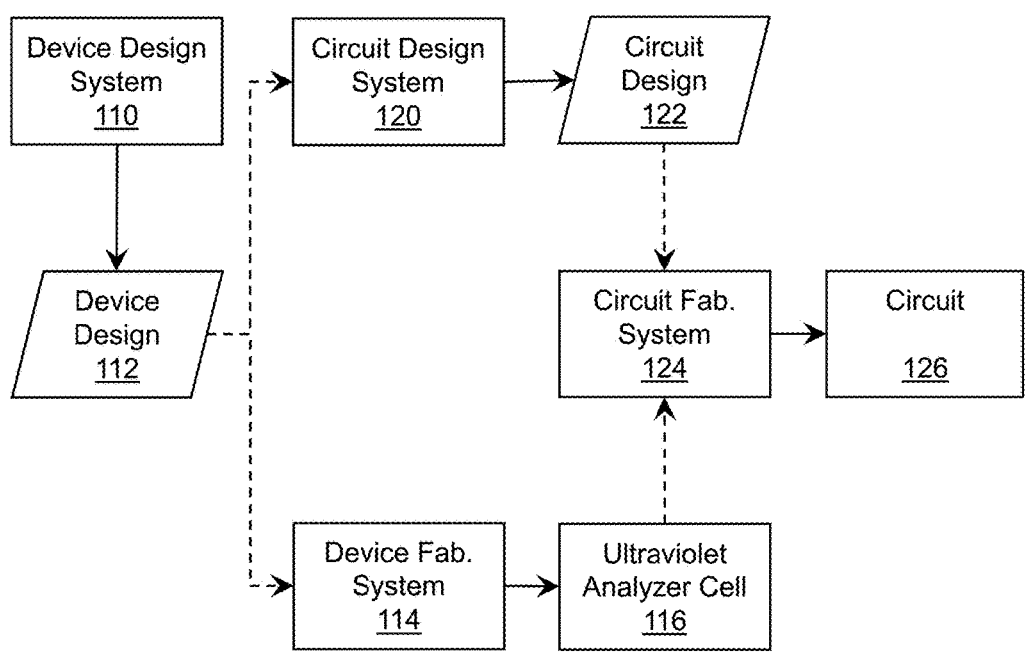
FIG. 13 shows an illustrative flow diagram for fabricating a circuit according to an embodiment.

While shown and described herein as an ultraviolet analyzer cell and various systems including one or more of such ultraviolet analyzer cells, it is understood that aspects of the invention further provide various alternative embodiments. For example, in one embodiment, the invention provides a method of designing and/or fabricating a circuit that includes one or more of the ultraviolet analyzer cells designed and fabricated as described herein. To this extent, FIG. 13 shows an illustrative flow diagram for fabricating a circuit 126 according to an embodiment. Initially, a user can utilize a device design system 110 to generate a device design 112 for an ultraviolet analyzer cell as described herein. The device design 112 can comprise program code, which can be used by a device fabrication system 114 to generate a set of physical ultraviolet analyzer cells 116 according to the features defined by the device design 112. Similarly, the device design 112 can be provided to a circuit design system 120 (e.g., as an available component for use in circuits), which a user can utilize to generate a circuit design 122 (e.g., by connecting one or more inputs and outputs to various devices included in a circuit). The circuit design 122 can comprise program code that includes an ultraviolet analyzer cell designed as described herein. In any event, the circuit design 122 and/or one or more physical devices 116 can be provided to a circuit fabrication system 124, which can generate a physical circuit 126 according to the circuit design 122. The physical circuit 126 can include one or more ultraviolet analyzer cells 116 designed as described herein.

In another embodiment, the invention provides a device design system 110 for designing and/or a device fabrication system 114 for fabricating an ultraviolet analyzer cell 116 as described herein. In this case, the system 110, 114 can comprise a general purpose computing device, which is programmed to implement a method of designing and/or fabricating the ultraviolet analyzer cell 116 as described herein. Similarly, an embodiment of the invention provides a circuit design system 120 for designing and/or a circuit fabrication system 124 for fabricating a circuit 126 that includes at least one ultraviolet analyzer cell 116 designed and/or fabricated as described herein. In this case, the system 120, 124 can comprise a general purpose computing device, which is programmed to implement a method of designing and/or fabricating the circuit 126 including at least one ultraviolet analyzer cell 116 as described herein.

In still another embodiment, the invention provides a computer program fixed in at least one computer-readable medium, which when executed, enables a computer system to implement a method of designing and/or fabricating an ultraviolet analyzer cell as described herein. For example, the computer program can enable the device design system 110 to generate the device design 112 as described herein. To this extent, the computer-readable medium includes program code, which implements some or all of a process described herein when executed by the computer system. It is understood that the term "computer-readable medium" comprises one or more of any type of tangible medium of expression, now known or later developed, from which a stored copy of the program code can be perceived, reproduced, or otherwise communicated by a computing device.

In another embodiment, the invention provides a method of providing a copy of program code, which implements some or all of a process described herein when executed by a computer system. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a device design system 110 for designing and/or a device fabrication system 114 for fabricating an ultraviolet analyzer cell as described herein. In this case, a computer system can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

Figure 14:
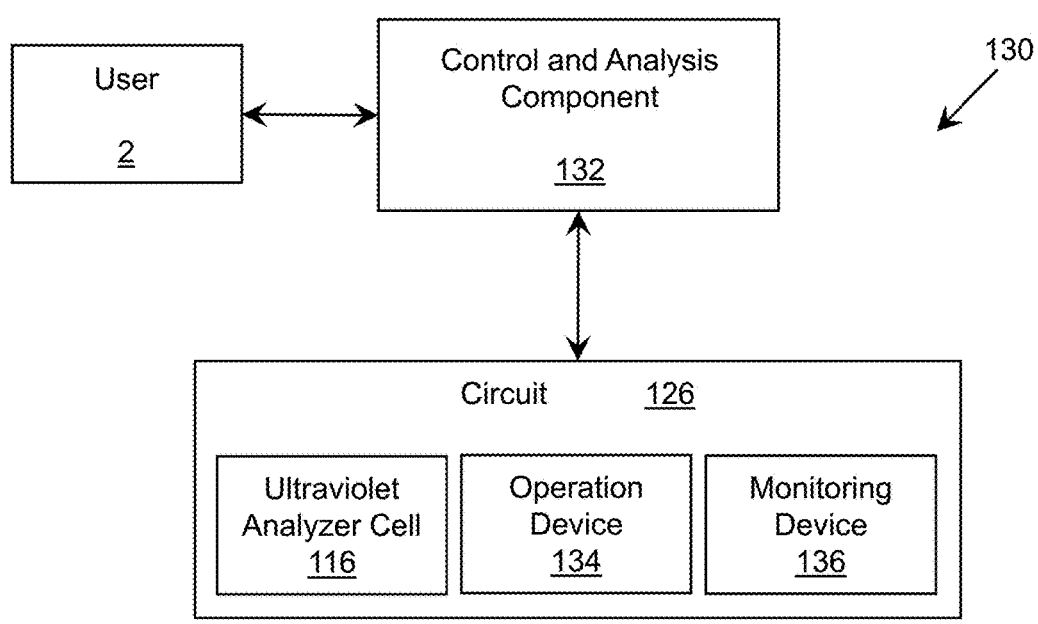
FIG. 14 shows an illustrative analyzer system according to an embodiment.

As discussed herein, the ultraviolet analyzer cell can be operated to acquire data on a medium, which can be analyzed to determine one or more attributes of the content of the medium. To this extent, FIG. 14 shows an illustrative analyzer system 130 according to an embodiment. The analyzer system 130 includes a control and analysis component 132, which can comprise, for example, a computing system configured to (e.g., a set of computing devices programmed to) operate a circuit 126 and analyze data acquired from the circuit 126 to evaluate a medium as described herein. A user 2 (e.g., a human user or another computer system), can interact with the control and analysis component 132 to affect the operation of the analyzer system 130 (e.g., select one or more options, start/stop analysis) and/or utilize the results of the analysis.

During operation of the analyzer system 130, the control and analysis component 132 can operate a set of operation devices 134 (e.g., transistors, current sources, voltage sources, medium flow devices, and/or the like), and acquire data from a set of ultraviolet analyzer cells 116 and/or a set of monitoring devices 136 included in the circuit 126. Illustrative monitoring devices 136 can include one or more thermistors, a set of UV detectors irradiated through a constant material (e.g., for differential analysis), flow meters, gas meters, and/or the like. The control and analysis component 132 can process the data to determine one or more attributes of the medium and/or adjust one or more aspects of the operation of the circuit 126 using any solution.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An ultraviolet analyzer cell comprising:
   an ultraviolet photodetector;
   a solid state light source configured to emit ultraviolet light, wherein at least some ultraviolet light emitted by the solid state light source passes through an analyzer active gap and irradiates a light sensing surface of the ultraviolet photodetector, wherein the ultraviolet photodetector and the solid state light source are monolithically integrated; and
   an insulating layer covering exposed surfaces of the analyzer active gap, wherein the insulating layer is transparent to the ultraviolet light emitted by the solid state light source, and wherein the insulating layer only partially fills the analyzer active gap.

2. The analyzer cell of claim 1, wherein a first side of the analyzer active gap is formed by the ultraviolet photodetector and a second side of the analyzer active gap is formed by the solid state light source.

3. The analyzer cell of claim 1, further comprising a substrate, wherein the ultraviolet photodetector and the solid state light source are formed on the substrate.

4. The analyzer cell of claim 3, wherein the ultraviolet photodetector is formed on the substrate and the solid state light source is formed on the photodetector, wherein the analyzer active gap extends under a portion of the solid state light source.

5. The analyzer cell of claim 4, wherein the photodetector is at least one of: a p-n junction diode, a multiple quantum well diode, a reverse-biased solid state light source, or a photoresistor.

6. The analyzer cell of claim 3, wherein the ultraviolet photodetector is formed on the substrate and the solid state light source is formed on the substrate adjacent to the ultraviolet photodetector, wherein the analyzer active gap physically separates the ultraviolet photodetector from the solid state light source.

7. The analyzer cell of claim 6, wherein the ultraviolet photodetector and the solid state light source are formed of semiconductor heterostructures having substantially the same layer structure.

8. The analyzer cell of claim 1, further comprising:
   a second ultraviolet photodetector, wherein at least some ultraviolet light emitted by the solid state light source passes through a differential gap and irradiates a light sensing surface of the second ultraviolet photodetector; and
   a gap filling material completely filling the differential gap.

9. The analyzer of claim 1, wherein the ultraviolet photodetector surrounds side surfaces of the solid state light source.

10. The analyzer cell of claim 1, further comprising:
    a first substrate having a first surface on which the ultraviolet photodetector is located and a second surface located opposite the first surface;
    a second substrate having a first surface on which the solid state light source is located and a second surface located opposite the first surface, wherein the second surface of the first substrate is bonded to the second surface of the second substrate;
    a set of channels formed in at least one of the first substrate or the second substrate, wherein the set of channels form the analyzer active gap.

11. The analyzer cell of claim 10, further comprising an ultraviolet reflective surface located adjacent to the set of channels at an interface between the first substrate and the second substrate.

12. An integrated ultraviolet analyzer comprising:
    a set of ultraviolet analyzer cells, each ultraviolet analyzer cell in the set of ultraviolet analyzer cells including:
        an ultraviolet photodetector; and
        a solid state light source configured to emit ultraviolet light, wherein at least some ultraviolet light emitted by the solid state light source passes through an analyzer active gap including a medium and irradiates a light sensing surface of the ultraviolet photodetector, wherein the ultraviolet photodetector and the solid state light source are monolithically integrated; and
    a circuit for operating the set of ultraviolet analyzer cells to evaluate the medium.

13. The analyzer of claim 12, wherein at least one of the ultraviolet analyzer cells in the set of ultraviolet analyzer cells further includes a monolithically integrated transistor configured to modulate an electrical signal applied to a bias contact of the solid state light source.

14. The analyzer of claim 12, wherein at least one of the ultraviolet analyzer cells in the set of ultraviolet analyzer cells further includes a monolithically integrated transistor configured to at least one of: amplify or transform, a signal received from a bias contact for the ultraviolet photodetector.

15. The analyzer of claim 12, wherein at least one of the ultraviolet analyzer cells in the set of ultraviolet analyzer cells further includes a second ultraviolet photodetector monolithically integrated with the ultraviolet photodetector and the solid state light source, wherein at least some ultraviolet light emitted by the solid state light source passes through the differential gap and irradiates a light sensing surface of the second ultraviolet photodetector, wherein a gap filling material completely fills the differential gap.

16. The analyzer of claim 12, wherein at least one of the ultraviolet analyzer cells in the set of ultraviolet analyzer cells further includes a monolithically integrated thermistor.

17. An integrated ultraviolet analyzer comprising:
   an ultraviolet analyzer cell including:
      a substrate;
      an ultraviolet photodetector formed on a first side of the substrate; and
      a solid state light source formed on the first side of the substrate, wherein at least some ultraviolet light emitted by the solid state light source passes through an analyzer active gap and irradiates a light sensing surface of the ultraviolet photodetector, wherein the analyzer active gap physically separates the ultraviolet photodetector from the solid state light source; and
   a circuit for operating the ultraviolet analyzer cell to evaluate a medium present in the analyzer active gap.

18. The analyzer of claim 17, wherein the analyzer active gap is formed by a set of channels located on a second side of the substrate located opposite the first side of the substrate, and wherein the ultraviolet analyzer cell further includes a reflective surface located immediately adjacent to the second side of the substrate.

19. The analyzer of claim 18, further comprising:
   a plurality of channels located prior to the ultraviolet analyzer cell, wherein at least two of the plurality of channels merge into the set of channels prior to the ultraviolet analyzer cell; and
   means for concurrently delivering a plurality of media using the plurality of channels, wherein the ultraviolet analyzer cell acquires data for evaluating at least one attribute of the combined media.

20. The analyzer of claim 17, wherein the ultraviolet photodetector and the solid state light source are formed of group III nitride semiconductor heterostructures having substantially the same layer structure.

* * * * *